US010306124B1

(12) United States Patent
Rodriquez, Jr.

(10) Patent No.: US 10,306,124 B1
(45) Date of Patent: May 28, 2019

(54) CAMERA VIEWING ATTACHMENT AND DISPLAY SYSTEM FOR LOW-SPEED DENTAL HANDPIECE

(71) Applicant: John Jesus Rodriquez, Jr., The Woodlands, TX (US)

(72) Inventor: John Jesus Rodriquez, Jr., The Woodlands, TX (US)

( * ) Notice: Subject to any disclaimer, the term of this patent is extended or adjusted under 35 U.S.C. 154(b) by 281 days.

(21) Appl. No.: 15/406,624

(22) Filed: Jan. 13, 2017

(51) Int. Cl.
| | |
|---|---|
| *H04N 5/20* | (2006.01) |
| *A61B 1/00* | (2006.01) |
| *A61B 1/05* | (2006.01) |
| *H04N 5/225* | (2006.01) |
| *H04N 5/232* | (2006.01) |
| *G03B 17/56* | (2006.01) |
| *A61B 1/06* | (2006.01) |
| *A61B 1/24* | (2006.01) |
| *A61C 1/08* | (2006.01) |
| *A61C 3/02* | (2006.01) |

(52) U.S. Cl.
CPC ....... *H04N 5/2257* (2013.01); *A61B 1/00018* (2013.01); *A61B 1/00032* (2013.01); *A61B 1/00039* (2013.01); *A61B 1/00045* (2013.01); *A61B 1/051* (2013.01); *A61B 1/053* (2013.01); *A61B 1/0684* (2013.01); *A61B 1/24* (2013.01); *A61C 1/088* (2013.01); *A61C 3/02* (2013.01); *G03B 17/561* (2013.01); *H04N 5/2253* (2013.01); *H04N 5/2254* (2013.01); *H04N 5/2256* (2013.01); *H04N 5/23212* (2013.01); *H04N 5/23293* (2013.01); *H04N 2005/2255* (2013.01)

(58) Field of Classification Search
CPC .... H04N 5/2257; A61B 1/00032; A61B 1/051
USPC ........................................................... 348/66
See application file for complete search history.

(56) References Cited

U.S. PATENT DOCUMENTS

| | | | |
|---|---|---|---|
| 5,049,070 A | 9/1991 | Ademovic | |
| 5,115,307 A | 5/1992 | Cooper | |
| 5,634,790 A | 6/1997 | Pathmanabhan | |
| 5,743,731 A | 4/1998 | Lares et al. | |
| 6,118,521 A * | 9/2000 | Jung | A61B 5/0088 250/227.14 |
| 6,419,484 B1 | 7/2002 | DaSilva et al. | |
| 6,958,766 B2 | 10/2005 | Cooper | |
| 2005/0171399 A1 * | 8/2005 | Rich | A61B 1/00048 600/112 |
| 2008/0021271 A1 * | 1/2008 | Pasero | A61B 1/00039 600/109 |
| 2012/0040305 A1 * | 2/2012 | Karazivan | A61B 1/00087 433/29 |

* cited by examiner

*Primary Examiner* — Jeffery A Williams
(74) *Attorney, Agent, or Firm* — Mary J. Gaskin

(57) ABSTRACT

A system providing a removable camera attachment for a low-speed dental handpiece and a cavity excavation viewing system. The camera viewing attachment provides a silicone-encased camera board with a lens that magnifies the cavity preparation site and an LED that illuminates the site. Visual information is transmitted to a viewing screen housed in a portable monitor. Because the low-speed dental handpiece does not use water, the images produced by the camera are clear. The system significantly improves a dentist's ability to assess the complete removal of decay and its proximity to a patient's nerve. The system can also be used in performing a root canal.

2 Claims, 4 Drawing Sheets

CAMERA VIEWING ATTACHMENT AND DISPLAY SYSTEM FOR LOW-SPEED DENTAL HANDPIECE

FIELD OF THE INVENTION

The present invention relates to a camera attachment for a low-speed dental handpiece.

BACKGROUND OF THE INVENTION

Presently, dental imaging systems are used to image intraoral and extraoral photographs of before and after dental images and for work-in-progress images, as well as for charting lesions and lab communication. Such systems require a separate imaging camera that is used to take images for charting records. In order to use such an imaging handpiece, a dentist must discontinue working on a patient, set up an acquisition mode for the image that is to be taken, identify the image to be acquired and its angulation, take the image, identify what is captured and its orientation, then, if needed, continue working on the patient, repeating the process, as needed, in order to complete the imaging sequence for the treatment procedure, thereby ensuring complete removal of decay. Limitations of such a system include: the amount of time the process takes; having to interrupt the procedure for image acquisition; the difficulty in deciphering the lesion, surface or location in relation to the image orientation; and the increased magnification that is utilized by such a system, rendering it more difficult to see the area even when using dental loupes, for example.

Some cameras have been disclosed for use for intraoral viewing without being attached to a handpiece. As a result, they cannot provide information as the cavity preparation is occurring. Other inventions disclose high speed handpieces with an internal camera and a fiber optic lens. However, the water spray used with such handpieces during cavity preparation would significantly hinder a dentist's ability to view the preparation in real time.

These limitations inspired the development of the present invention, which provides an imaging capability to low-speed dental handpieces so that treatment can be seen in a magnified, real-time situation. Because low-speed dental handpieces do not require water for operation, the dentist's view is not adversely affected by water spray. Treatment would not have to be interrupted in order to check progress. Work in progress can be seen on a monitor as it occurs, thereby decreasing the amount of time it takes to check treatment progress using current technology. Magnification of the working field allows more accurate removal of tooth structure, decay, tartar, bone and lesions, as well as instrumentation of canals. Such an imaging system would improve the practitioner's ability to provide a higher level of care for his patients by supporting improved posture and reduced physical fatigue and increased accuracy of decay removal. It would also decrease chair time for the patient.

SUMMARY OF THE INVENTION

The present invention provides a camera attachment for a low-speed handpiece and cavity excavation viewing system. A dentist using the system can view, in real time, the cavity preparation area, thereby ensuring complete decay removal. The system provides magnification, which significantly improves the dentist's ability to assess the complete removal of decay and its proximity to a patient's nerve. The camera of the system can also be used by a dentist or root canal specialist to view the pulpal floor and shape, as well as canal orifices for root canal preparation using rotary files.

The camera viewing attachment includes a silicone-encased camera board with a lens and an LED (light-emitting diode) that illuminates the cavity preparation site, and which is mounted on the handpiece in a three-part adapter. Visual information about the cavity preparation area is transmitted from the camera lens to a viewing screen in a monitor, allowing for significant magnification and illumination of the cavity or access preparation.

The system of the present invention has many advantages. Because the camera attachment is located external to the handpiece, it can be easily removed, cleaned, sterilized, and replaced. The camera viewing attachment incorporates an LED, which increases the amount of available light on the cavity preparation area. The magnification provided by the camera unit significantly enhances viewing of the cavity preparation area. The viewing screen, which is connected to the camera board through a camera wiring harness, is part of a monitor, which houses the batteries that power the LED. Finally, the low-speed dental handpieces with which the system is used do not use water, so the images produced by the camera and displayed on the viewing screen are clear.

DESCRIPTION OF THE PREFERRED EMBODIMENT

Figure 1:
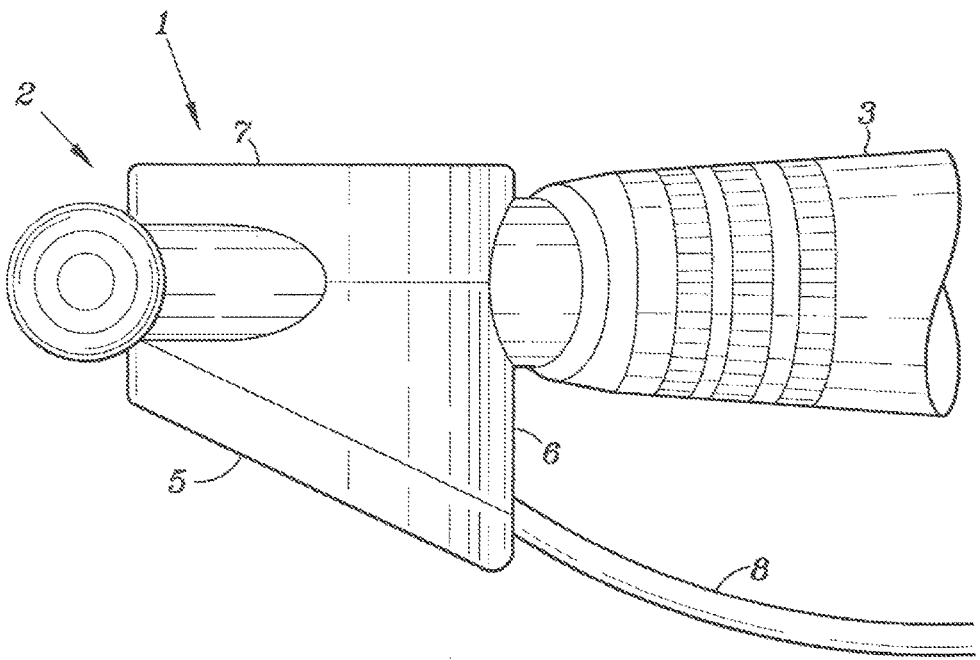
FIG. 1 is a top plan view showing the camera attachment of the present invention mounted on the drilling end of a low-speed dental handpiece.

As shown in FIG. 1, the removable camera viewing attachment 1 of the present invention is mounted on the drilling end 2 of a low-speed dental handpiece 3. The camera viewing attachment 1 that encloses a camera board (not seen in this view) has a camera board housing adapter 5, which connects to a camera board housing/handpiece adapter 6, which connects to a handpiece adapter/connector 7. The camera board housing adapter 5 and the camera board housing/handpiece adapter 6 encapsulate the camera board (not seen) and an end of the camera wiring harness 8 and are bolted together. The three adapters are made from a durable material such as aluminum, stainless steel, titanium, nylon, or a durable plastic. The camera board housing/handpiece adapter 6 and the handpiece adapter/connector 7 fit around the drilling end 2 of a low-speed handpiece 3 and are bolted together.

Figure 2:
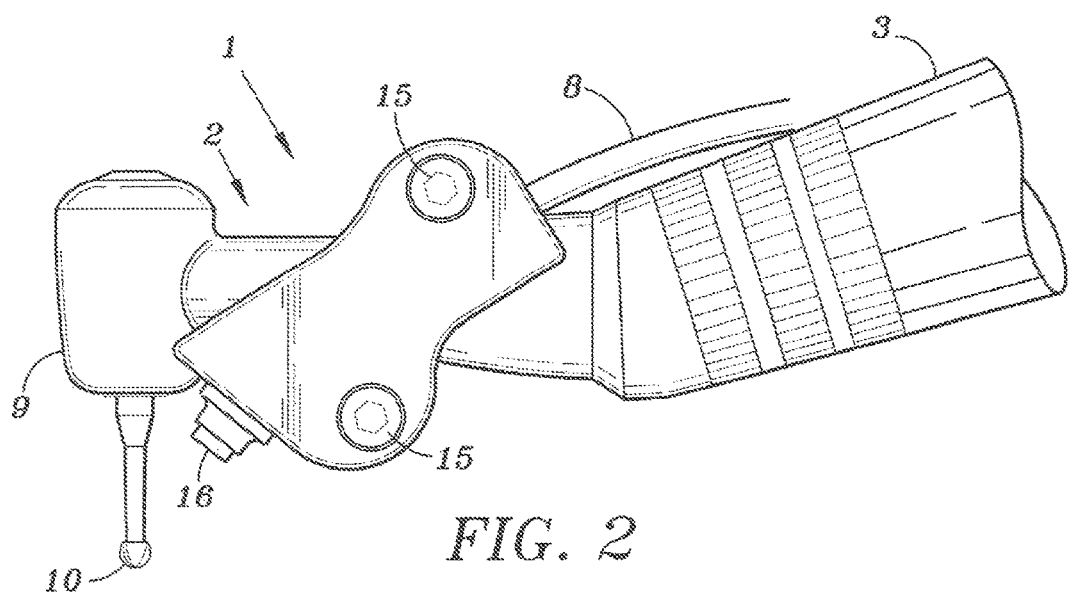
FIG. 2 is a side plan view showing the camera attachment of the present invention mounted on the drilling end of a low-speed dental handpiece.

The side plan view of FIG. 2 shows the camera viewing attachment 1 of the present invention mounted on the drilling end 2 of a low-speed dental handpiece 3. The drill head 9 with an excavating bur 10 extending therefrom can be seen, along with the camera wiring harness 8 extending from the camera board (not seen). Fixating hex bolts 15 hold the three pieces of the camera viewing attachment together on the drilling end 2 of the low-speed dental handpiece 3. The camera lens 16, which has automatic focus and magnification features, can be seen angulating toward the excavating bur 10.

Figure 3:
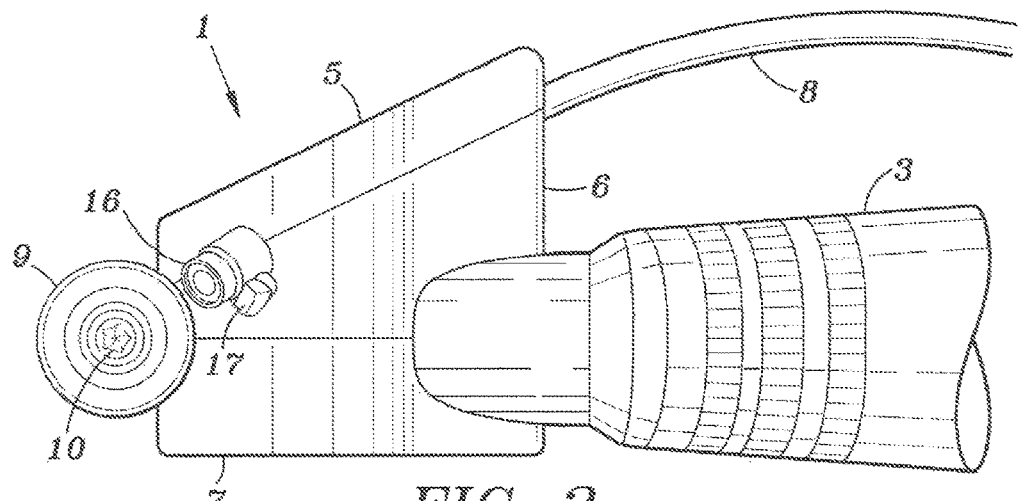
FIG. 3 is a bottom plan view showing the camera attachment of the present invention mounted on the drilling end of a low-speed dental handpiece.

The bottom plan view of FIG. 3 shows the camera viewing attachment 1 of the present invention mounted on the low-speed dental handpiece 3. The three adapters of the camera viewing attachment 1, the camera board housing adapter 5, the camera board housing/handpiece adapter 6, and the handpiece adapter/connector 7 are bolted together, encapsulating the camera board (not shown). The camera lens 16, which is 6 mm in diameter with 100K pixel resolution and a built-in infrared cut filter, operates off of low voltage 3.3 V. It has a built-in LED (light-emitting diode) 17 with on/off controllability. The camera lens is angled at 160 degrees in order to allow the dentist working in the cavity preparation site to view the excavating bur 10 while it is removing decay.

Figure 4:
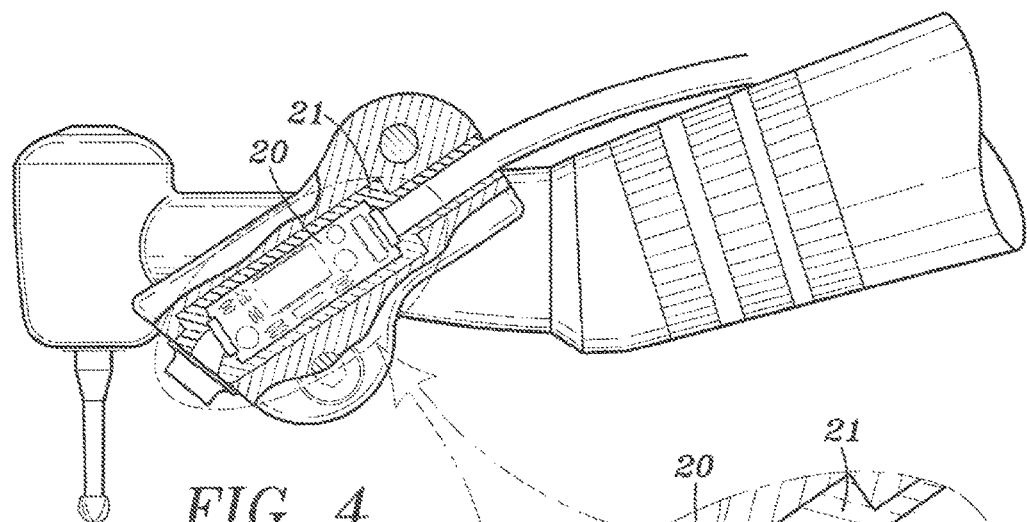
FIG. 4 is the side plan view of FIG. 2, showing a partial sectional view of the camera attachment of the present invention.
Figure 4A:
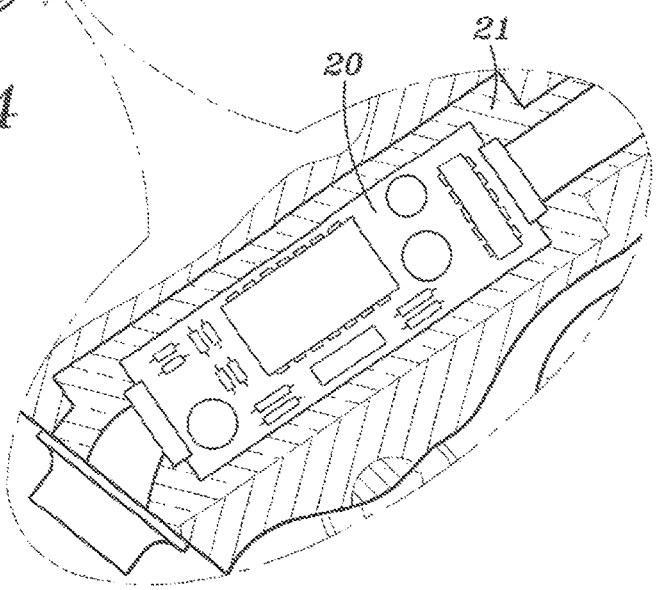
FIG. 4A is an enlargement of a portion of the sectional view of FIG. 4.

As can be seen in FIG. 4 and the enlarged partial view in FIG. 4A, the camera board 20 is encased in a silicone layer 21 in order to protect it from the wet oral cavity and disinfectants. The camera board 20, utilizing a sensor, integrates signal processing, timing and control circuitry on a single chip. The camera wiring harness 8 will transmit information from the camera board 20 to the monitor (not seen in this figure).

Figure 5:
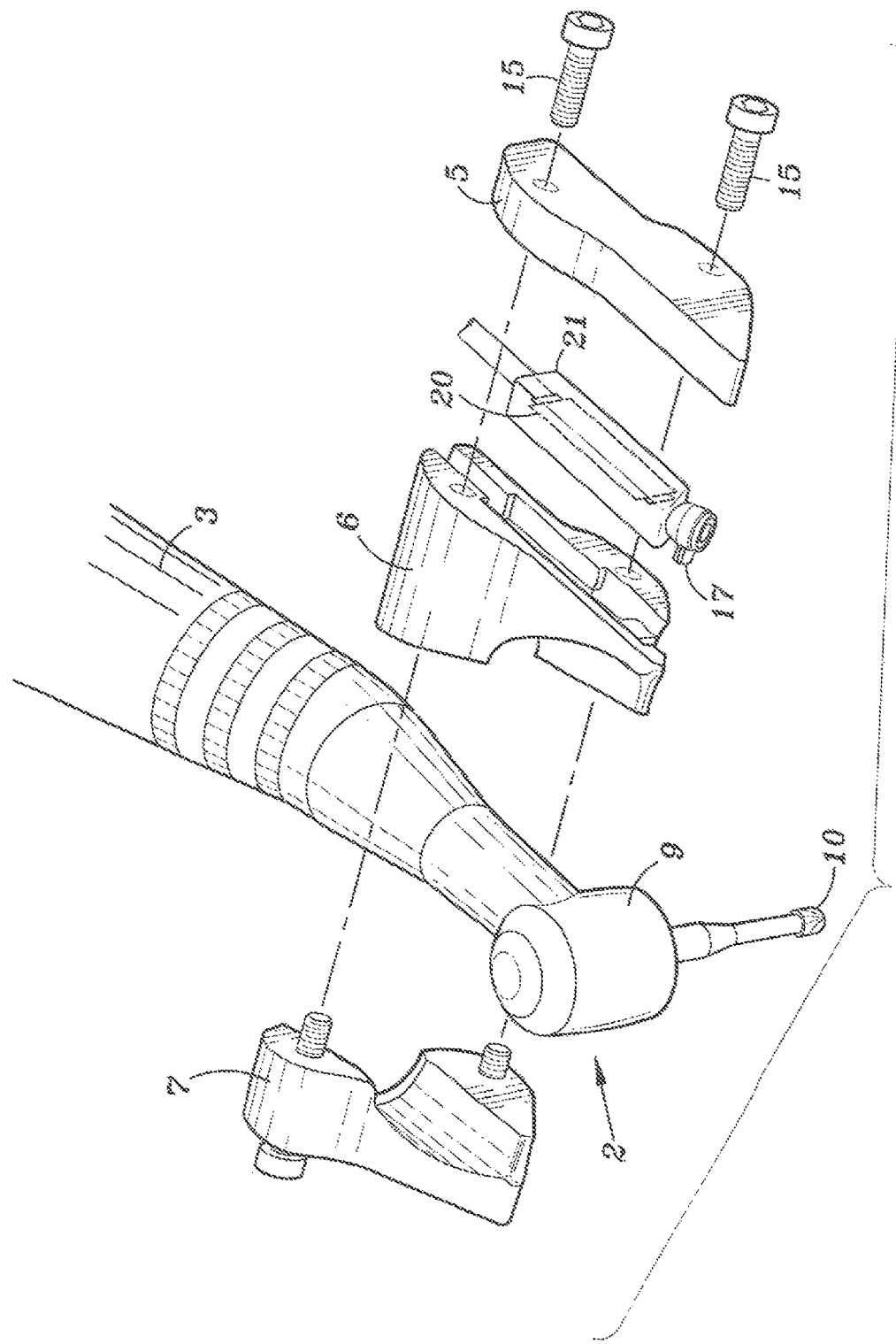
FIG. 5 is an exploded view of an angled perspective front view of the camera attachment of the present invention, showing how the parts of the camera attachment are assembled when mounted on the drilling end of a low-speed dental handpiece.

The exploded view of FIG. 5 shows how the camera viewing attachment 1 is assembled. The handpiece adapter/connector 7 is aligned with the camera board housing/handpiece adapter 6, each piece on one side of the drilling end 2 of a low-speed dental handpiece 3, and then bolted together with hex bolts 15, which are inserted through receiving holes in the adapters. The camera board 20 is aligned with the outer side of the camera board housing/handpiece adapter 6, and the camera board housing adapter is aligned on the other side of the camera board 20. Hex bolts 15 are inserted through the receiving holes in the adapters in order to bolt the adapters together. All the hex bolts 15 are removable, so that the camera viewing attachment 1 can be removed from the low-speed dental handpiece 3.

Figure 6:
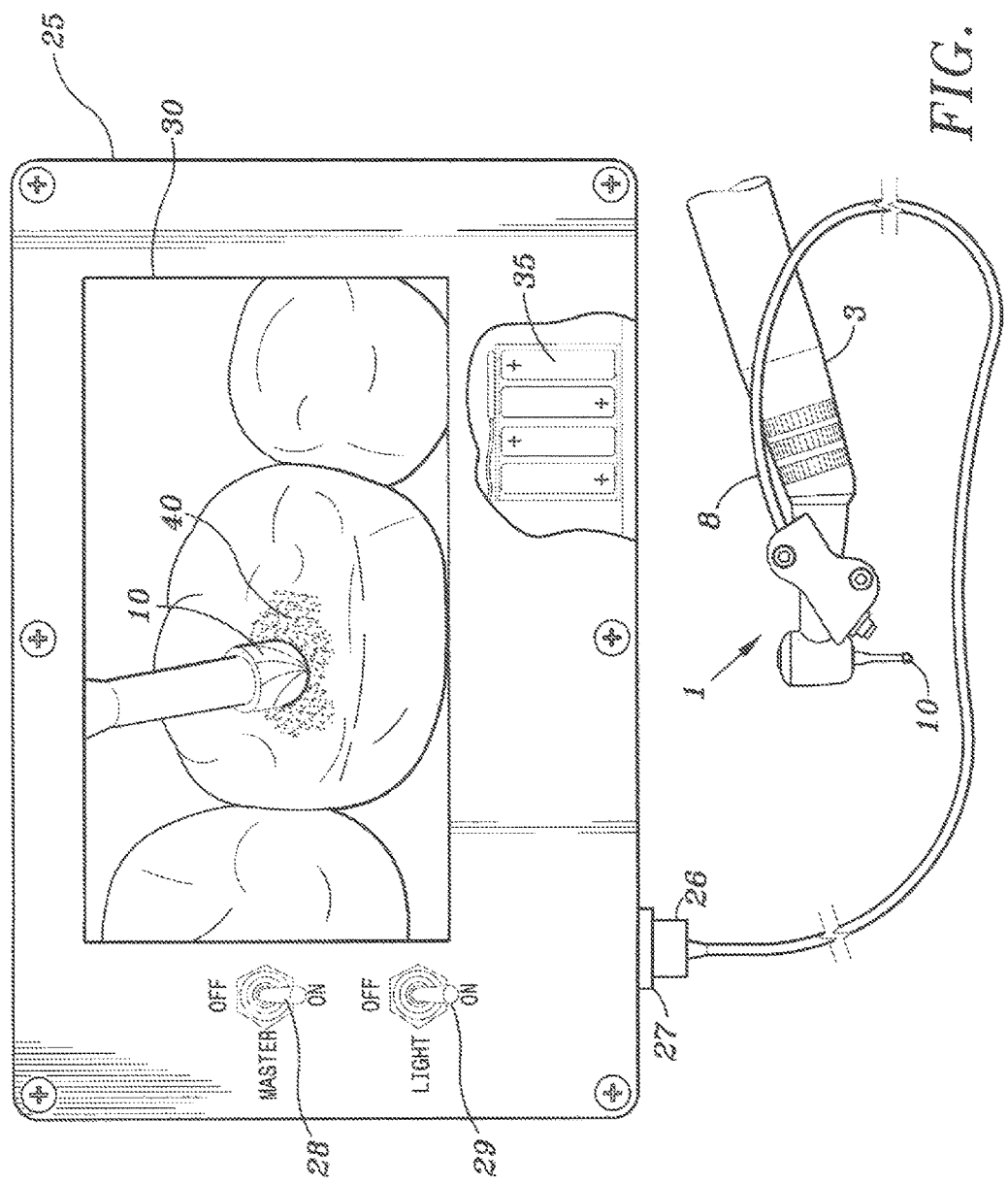
FIG. 6 is a representational view showing the information transmitted by the camera attachment of the present invention from a cavity preparation site to a viewing screen.

The monitor 25 shown in FIG. 6 receives information from the camera board 20 (not shown) through camera wiring harness 8, which is connected to the monitor 25 by inserting a 5-pin XLR adapter 26 into receptacle 27. The monitor 25 has a master on/off switch 28, as well as an LED on/off switch 29 to allow the dentist to turn the LED (not shown in this view) on or off. The LED emits light that is reflected back to the camera lens, which creates the image on the camera sensor and sends an analog signal through the wiring harness 8 to the viewing screen 30 for analog video display in the monitor 25. The viewing screen 30 allows the dentist to view, in real time, the cavity preparation site 31 in a patient's tooth 32, as the excavating bur is activated. The monitor is portable, as the unit uses direct current power provided by batteries 35, for instance, 8 AA batteries can be used.

In using the present invention, the dentist will place the monitor in a convenient viewing location and turn on the master switch and the LED. Using the low-speed dental handpiece, on which the camera viewing attachment is mounted, the dentist will activate the excavating bur in order to remove decay from a patient's cavity. As the decay is removed from the cavity, the dentist is able to see a magnified, real-time image of his work, and he is better able to determine complete removal of decay without having to remove his handpiece from the preparation site. This reduces the amount of decay that may otherwise be left behind due to his not having magnification to improve his view of the decay. The clinician is better able to see microscopic nerve exposures, allowing for a better treatment decision and prognosis. If a tooth requires a root canal, the excavation bur can be used to access the pulpal chamber, and then can be replaced with a root canal file for enhanced viewing of the canals during canal instrumentation.

Although the description contains many specifics, these should not be construed as limiting the scope of the invention, but merely as providing illustrations of the presently preferred embodiment of this invention.

I claim:

1. A system for use with a low-speed dental handpiece having a drilling end with an excavation bur, the system comprising:
   (a) a camera board comprising a lens, a sensor, a chip, and an LED (light-emitting diode), wherein the camera board is encased in a layer of silicone;
   (b) means for removably mounting the camera board onto the drilling end of the dental handpiece;
   (c) an image display system comprising a monitor, means for receiving information from the camera board, a viewing screen, power means, and activation switches;
   (d) means for transmitting information from the camera board to the monitor.

2. A system for use with a low-speed dental handpiece having a drilling end with an excavation bur, the system comprising:
   (a) a camera board comprising a lens, a sensor, a chip, and an LED (light-emitting diode);
   (b) means for removably mounting the camera board onto the drilling end of the dental handpiece;
   (c) an image display system comprising a monitor, means for receiving information from the camera board, a viewing screen, power means, and activation switches;
   (d) means for transmitting information from the camera board to the monitor, wherein the means for removably mounting the camera board onto the drilling end of the dental handpiece comprises adapters configured to encapsulate the camera board and to fit around the drilling end of the dental handpiece, the adapters being constructed from a durable material selected from the group consisting of aluminum, stainless steel, titanium, nylon, and a durable plastic, and wherein the adapters have receiving holes and which further comprise bolts for insertion through the receiving holes and affixing the adapters onto the drilling end of the dental handpiece.

* * * * *